US00PP11041P

United States Patent [19]

Jacob

[11] Patent Number: Plant 11,041

[45] Date of Patent: Aug. 24, 1999

[54] PYRUS COMMUNIS DWARFING ROOTSTOCK NAMED 'RHENUS 1'

[76] Inventor: Helmut B. Jacob, Nachtigallenweg 15, D-65366 Geisenheim, Germany

[21] Appl. No.: 08/961,307

[22] Filed: Oct. 30, 1997

[51] Int. Cl.[6] ..... A01H 5/00

[52] U.S. Cl. ..... Plt./179

[58] Field of Search ..... Plt./36, 37, 35.2, Plt./38.1, 38.2, 39, 40, 41.1, 41.2, 41.3, 41.4, 42.1, 43.1, 43.2, 43.3, 179, 183, 184

[56] References Cited

PUBLICATIONS

Jacob, H., Pyrodwarf: Eine neue Klonunterlage fuer den intensiven Birnenanbau. Erwerbsobstbau 38, 166–169, 1996.

UPOV ROM 1998/01, Plant Variety Database, GTI Jouve Retrieval Software, citation for 'Pyrodwarf', Feb. 1994.

*Primary Examiner*—Howard J. Locker
*Assistant Examiner*—Anne Marie Grünberg
*Attorney, Agent, or Firm*—Klarquist Sparkman Campbell Leigh & Whinston, LLP

[57] ABSTRACT

A new and distinct variety of *Pyrus communis* named 'Rhenus 1' that is compatible as a rootstock with all pear varieties tested and when used as a rootstock for pear varieties, causes dwarfing to a degree at least as great as quince A rootstock without significantly reducing fruit size, high yield efficiency, early yield (precocity), substantially uniform fruit size, high frost hardiness, no suckering, and good soil adaptation.

1 Drawing Sheet

BACKGROUND OF THE INVENTION

The present invention comprises a new dwarfing rootstock for pears (*Pyrus communis*) referred to by the varietal name 'Rhenus 1'. The federally registered trademark 'Pyrodwarf' is the brand name for marketing this plant in the United States.

Very few dwarfing rootstocks for pears are currently available. Clones of quince (*Cydonia oblonga*) are used by pear growers in maritime countries of northern Europe to provide vigor control, scion precocity, and good yield efficiency. However, quince is incompatible with many commercial pear varieties, including 'Bartlett'. Moreover, since most quince clones exhibit poor tolerance to winter cold, growers in areas with cold winters must employ Pyrus species rootstocks, most of which are invigorating.

Although selections from the cross between the pear varieties 'Old Home' (unpatented, believed to be publicly available) and 'Farmingdale' (OHxF) (unpatented, believed to be publicly available) have been investigated as rootstocks for pear varieties, none appears to have significant size-controlling ability, particularly when grown on deep loam or clay soils with good moisture supply.

Pyrus rootstocks are usually extremely difficult to propagate by conventional vegetative methods. As a result, about one-half are propagated from seed. They also often stimulate poor scion precocity and cause smaller fruit size.

The new variety was selected by me in a cultivated area in a orchard at the Research Station of Viticulture and Horticulture in Geisenheim, Germany. Pear varieties 'Old Home' (female) and 'Bonne Louise d'Avranches' (male) (unpatented, believed to be publicly available) were cross-pollinated and 2500 of the resulting seeds were germinated. In a first evaluation, two pear varieties, 'Bartlett' and 'Doyenne de Comice' were grafted to the seedlings. The grafted seedlings then were evaluated as rootstocks according to the following criteria: trunk cross-sectional area, cumulative marketable yield, yield efficiency, blossoming, tree health, compatibility, frost hardiness, suckering, soil adaptation. Twenty-two seedling clones that displayed the best results were selected for further testing. The selected seedling clones were cut below the grafting union to produce root suckers for asexual reproduction and virus indexing. 'Rhenus 1' was selected from among the twenty-two clones as giving the best results.

'Rhenus 1' has not been observed under all possible environmental conditions and its phenotype may vary significantly with variations in environment such as temperature, light intensity, and day length, without any variation in genotype. However, the following unique combination of characteristics relating to the use of 'Rhenus 1' as a rootstock for pear varieties, distinquish 'Rhenus 1' from all other pear varieties of which I am aware: (1) causes dwarfing of pear varieties to a degree at least as great as quince A rootstock without significantly reducing fruit size; (2) compatible as a rootstock with all pear varieties tested; (3) high yield efficiency; (4) early yield (precocity); (5) substantially uniform fruit size; (6) high frost hardiness; (7) no suckering; (8) and good soil adaptation. These characteristics are established and transmitted through succeeding asexual propagations.

Asexual reproduction of 'Rhenus 1' is accomplished, for example, by tissue culture; softwood and hardwood cuttings, e.g., using 2000 ppm indole-3-butyric acid (IBA) (quick dipping) by the "methode Trefoise" (R. Trefoise, "Description des techniques de bouturage feuille des nouveaux sujets porte-greffe nanifiants dur cerisier," *Note technique du Centre de Recherches Agronomiquies de l'Etat Gembloux*, No. 10/50, Septembre 1988, I.S.S.N. 0771-0607, 1988); and by stool bed propagation (layering).

BRIEF DESCRIPTION OF THE DRAWINGS

The following drawings are photographs of 'Rhenus 1' taken at the Research Station of Viticulture and Horticulture in Geisenheim, Germany, in September 1995.

DETAILED DESCRIPTION OF THE PREFERRED EMBODIMENTS

The following is a detailed description of the invention based on plants grown at the Research Station of Viticulture and Horticulture in Geisenheim, Hessen, Germany (hereinafter, "the Research Station"). Color descriptions and other terminology are used herein in accordance with ordinary dictionary significance unless otherwise noted with reference to The Royal Horticultural Society Colour Chart (R.H.S.). It should be noted that color does vary with time of year, lighting conditions, and soil and nutrient conditions. For example, leaf colors tend to be brighter green if the plants are grown in soil with greater nitrogen concentrations, and to be more yellow when grown in soil containing lesser amounts of nitrogen.

All trees of the 'Rhenus 1' variety, insofar as I have been able to observe them, have been identical in all the characteristics described below.

Propagation: Holds to distinguishing characteristics through succeeding propagation by rooted cuttings.

Figure 1:
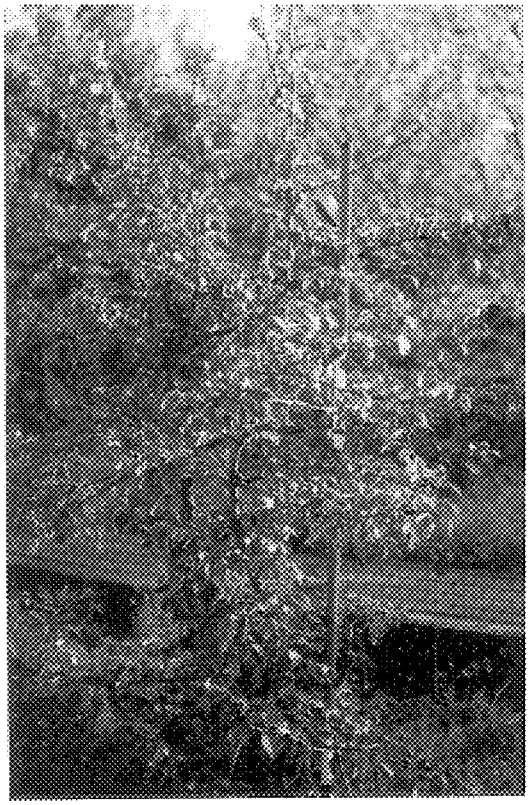
FIG. 1 is a view of five-year-old nonpruned specimen of 'Rhenus 1' (height: 2.5 m).
Figure 4:
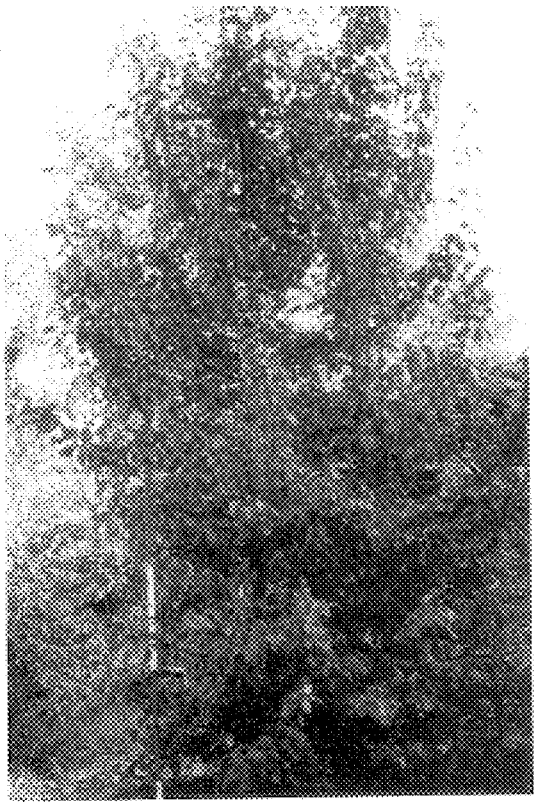
FIG. 4 is a view of five-year-old non-grafted nonpruned seeding specimen of 'Bartlett' (height: 6.5 m) which, when compared with FIG. 1, illustrates an example of the growth rate of 'Pyrodwarf' compared to that of 'Bartlett' trees.

Tree (nongrafted):

*Trunk.*—Size: Dwarf to medium. Height: After five years, nongrafted 'Rhenus 1' trees range from 2.0 to 2.5 m (FIG. 1 shows a five-year old nonpruned specimen with a height of 2.5 m.); by comparison, vigorous pear trees, e.g., 'Bartlett', are commonly 5 to 7 m when grown under the same conditions (FIG. 4 shows a five-year-old non-pruned specimen of a non-grafted seedling 'Bartlett' pear tree with a height of 6.5 m. which, when compared to FIG. 1, the 'Pyrodwarf' tree of FIG. 1, provides a visual example of a comparison of the vigor of 'Pyrodwarf' to 'Bartlett' trees). Circumference: After five years, nongrafted 'Rhenus 1' trees are about 80 mm, grafted trees about 71 mm. Bark color: Bright gray-brown. Surface color: Gray-brown (2 year old trunk bark color like R.H.S. 199A). Surface texture: Smooth.

*Form.*—Spread upright.

Figure 2:
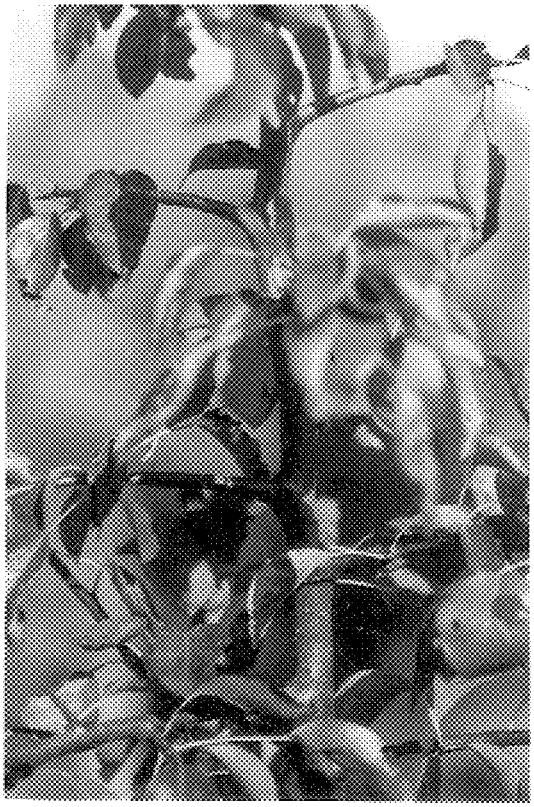
FIG. 2 is a detailed view of the specimen of FIG. 1 showing branches and spurs of 'Rhenus 1'.
Figure 3:
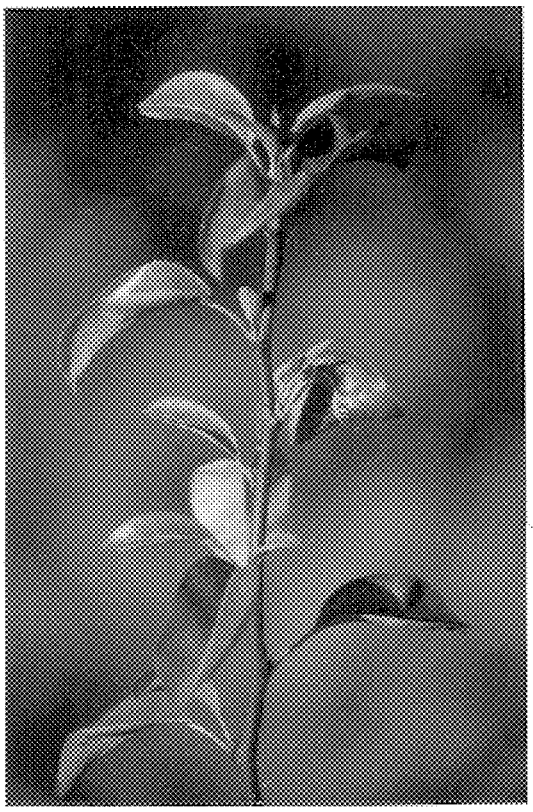
FIG. 3 is an enlarged view of a branch and leaves of 'Rhenus 1'.

*Branches* (*see* FIGS. 2 and 3).—Size: Small, slight. Surface texture: Smooth. Bark color: Red-brown to gray-brown. New growth color: Bright green. Mature one year growth color: Red-brown (like R.H.S. 100B for bark of mature one year branches taken in the fall from a 'Pyrodwarf' plant growing in McMinnville, Oreg. By mature one year branches, it is meant branches that have grown throughout the summer of a growing season. Internode length: 18–25 mm. Lenticels: Yellow-white, small, circular on mature one year old branches.

*Leaves* (*see* FIG. 3).—Size: Small. Length averages 50–60 mm, including the petiole. Width averages 28–32 mm. Surface texture: Normal for the species. Form: Linear-elongated. Color: Upper surface is bright to dark green (like R.H.S. 146A for leaves from a 'Pyrodwarf' plant growing in McMinnville, Oreg.). Lowwer surface is bright gray-green (like R.H.S. 147C for the leaves from a 'Purodwarf' plant growing in McMinnville, Oreg. Mid-vein: Size: average. Color: Yellow-green. Petiole: Length: Normal for species, 8–10 mm. Thickness: 0.3–0.5 mm. Color: yellow-green to brown (like R.H.S. 174A for fall leaves from a 'Pyrodwarf' plant growing in McMinnville, Oreg.). Leaf glands: none.

*Flowers and fruit.*—None in six years of observation.

Performance as rootstock when grafted:

*Growth characteristics.*—Between quince C and quince A in dwarfing capability.

*Root sprouts* (*suckering*).—None in seven years.

*Anchorage.*—Very good.

*Compatibility.*—Very good. No incompatibility observed with any pear variety.

*Fruit size.*—When used as a rootstock for 'Bartlett' pear, greater than 90% of the fruit being of good market size.

Soil adaptation and tolerance:

*Chlorosis.*—No problems observed.

*Wet.*—No problems observed.

Pathogen resistance: Moderately tolerant to fire blight. Very tolerant to powdery mildew.

'Rhenus 1' rootstock has been found to reduce scion shoot growth (e.g., as measured by trunk circumference) of commercially important pear varieties such as 'Bartlett'. As shown in Table 1 for 'Bartlett' scions grafted to 'Rhenus 1' and various other rootstocks, 'Rhenus 1' rootstock is about 50 percent more dwarfing than PY 2/33 rootstock (an unpatented, proprietary variety, also sometimes designated BU 2/33), about 33 percent more dwarfing than OHxF 333 rootstock, about 24 percent more dwarfing than quince A rootstock, and about 10 percent less dwarfing than quince C rootstock. It has been observed that the further the rootstock shank is exposed above ground, the greater the extent of dwarfing.

Moreover, 'Rhenus 1' does not significantly reduce fruit size. Fruit from 'Bartlett' trees grafted to 'Rhenus 1' rootstock is larger than fruit from 'Bartlett' grafted to quince A and grown under similar conditions. More than 90 percent of fruit from 'Bartlett' grown on 'Rhenus 1' rootstock is of good market size (as shown in Table 2, all fruit was 65 mm or larger).

In addition, 'Rhenus 1' rootstock confers precocity on grafted pear varieties, even though it has previously proven difficult to force precocity on pears. Pear varieties that are grafted to 'Rhenus 1' rootstock have a shorter juvenile stage, apparently shutting down vegetative growth early, and form fruit buds on the shoot tips. For example, 'Bartlett' pear trees grafted to 'Rhenus 1' rootstock can bear fruit in as little as three to four years, compared with seven years for self-rooted 'Bartlett' pear trees.

Based on our testing, 'Rhenus 1' is expected to be compatible with all varieties of *Pyrus communis* (Euroopean pears), *Pyrus pyrifolia* (Japanese pears), and *Pyrus ×bretscheideri* (Chinese pears).

Pear varieties grafted as scions to 'Rhenus 1' rootstock display early yield or precocity, i.e., the cumulative marketable yield of fruit of a pear variety grown on 'Rhenus 1' rootstock is significantly higher at years five or six than if the variety is self-rooted. For example, 'Bartlett' pear trees grafted to 'Rhenus 1' rootstock often bear fruit in about three to four years, compared with about seven years when self-rooted.

As shown in Table 1, the yield efficiency of 'Bartlett' pear trees grafted on 'Rhenus 1' rootstock is about 98 percent, 45 percent, 249 percent, and 32 percent higher than the yield efficiency of 'Bartlett' scions grafted on quince A (publicly available, unpatented), quince C (publicly available, unpatented), OHxF 333, and PY 2/33 rootstock, respectively.

'Rhenus 1' also displays high frost hardiness, i.e., is able to withstand cold winter temperatures (−15° C. for fifteen days) without substantial freezing damage.

Comparison Tables

Table 1 provides data regarding the growth (trunk circumference) and yield efficiency (or productivity) of 'Bartlett' grafted to 'Rhenus 1' and other rootstocks. Trunk circumference measurements are made 10–20 cm above the graft union on grafted trees. Table 2 provides data regarding fruit size grades and total fruit weight and number of 'Bartlett' grafted to 'Rhenus 1' and other rootstocks.

TABLE 1

Growth and Yield Efficiency of Bartlett Pears Grafted on Various Pear Rootstocks

| | Yield (kg) | | | | | Total Trunk Circum- | Yield |
|---|---|---|---|---|---|---|---|
| Rootstock | 1986 | 1987 | 1988 | 1989 | 1986–1989 | ference* (mm) | Effi-ciency** |
| EM QUINCE A | 0.0 | 1.7 | 11.1 | 14.2 | 27.0 | 105 | 25.7 |
| EM QUINCE C | 1.3 | 7.1 | 9.1 | 8.2 | 25.7 | 73 | 35.2 |
| OHxF 333 | 0.0 | 3.1 | 7.3 | 7.0 | 17.4 | 119 | 14.6 |

TABLE 1-continued

Growth and Yield Efficiency of Bartlett Pears Grafted on Various Pear Rootstocks

| | Yield (kg) | | | | | Total Trunk Circum- | Yield |
|---|---|---|---|---|---|---|---|
| Rootstock | 1986 | 1987 | 1988 | 1989 | 1986–1989 | ference* (mm) | Effi-ciency** |
| PY 2/33 | 11.3 | 14.4 | 17.1 | 19.2 | 62.0 | 160 | 38.7 |
| Rhenus 1 | 0.9 | 2.5 | 17.6 | 19.8 | 40.8 | 80 | 51.0 |

*Six years after planting $$\text{**Yield efficiency (kg/mm)} = \frac{\text{Total Yield 1986–1989}}{\text{Trunk circumference}} \times 100$$

TABLE 2

Fruit Size Grades of Bartlett Pears Grown on Various Pear Rootstocks

| | Number of Fruit in Various Size Grades* | | | | | | | | | Total Weight | Total Fruit |
|---|---|---|---|---|---|---|---|---|---|---|---|
| Rootstock | 45 | 50 | 55 | 60 | 65 | 70 | 75 | 80 | 85 | (kg) | Number |
| EM QUINCE A | 1 | 2 | 3 | 20 | 33 | 13 | 2 | 1 | 1 | 14.2 | 76 |
| EM QUINCE C | 2 | 5 | 19 | 21 | 3 | 2 | 0 | 0 | 0 | 8.2 | 52 |
| PY 2/33 | 0 | 2 | 2 | 22 | 25 | 20 | 21 | 3 | 1 | 19.2 | 96 |
| Rhenus 1 | 0 | 0 | 0 | 0 | 34 | 49 | 10 | 10 | 2 | 19.8 | 105 |

*Size grades given in mm. Year is 1989.

I claim:

1. A new and distinct variety of *Pyrus communis* Plant as herein shown and described.

* * * * *